(12) United States Patent
Turner

(10) Patent No.: US 10,773,071 B2
(45) Date of Patent: Sep. 15, 2020

(54) PUMP TUBE RETENTION MECHANISM

(71) Applicant: Spectrum Medical Ltd., Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 231 days.

(21) Appl. No.: 15/542,235

(22) PCT Filed: Jan. 8, 2016

(86) PCT No.: PCT/GB2016/050044
§ 371 (c)(1),
(2) Date: Jul. 7, 2017

(87) PCT Pub. No.: WO2016/113545
PCT Pub. Date: Jul. 21, 2016

(65) Prior Publication Data
US 2017/0354814 A1  Dec. 14, 2017

(30) Foreign Application Priority Data

Jan. 12, 2015  (GB) .................................. 1500422.9

(51) Int. Cl.
*A61M 39/28* (2006.01)
*F04B 43/12* (2006.01)
(Continued)

(52) U.S. Cl.
CPC .......... *A61M 39/287* (2013.01); *A61M 39/28* (2013.01); *A61M 39/285* (2013.01);
(Continued)

(58) Field of Classification Search
USPC ......................................................... 251/4–6
See application file for complete search history.

(56) References Cited

U.S. PATENT DOCUMENTS 2,197,310 A  4/1940  Lincoln
4,164,223 A  8/1979  Munib
(Continued)

FOREIGN PATENT DOCUMENTS

CH  707 421 A1  12/2012
GB  467288 A  6/1937
(Continued)

OTHER PUBLICATIONS

United Kingdom Intellectual Property Office, Search Report under Section 17, Application No. GB1500422.9, dated May 26, 2015, 1 page.
(Continued)

*Primary Examiner* — Daphne M Barry
(74) *Attorney, Agent, or Firm* — Sunstein LLP

(57) ABSTRACT

A clamp arrangement for retaining a flexible tube (18) during operation of a roller pump (10) for pumping fluid, the clamp arrangement comprising a pair of rotatable bobbins (24A, 24B, 26A, 26B) mounted adjacent to each other. Each bobbin (24A, 24B, 26A, 26B) has a tapered groove (30), formed partially around a cylindrical surface of the bobbin (24A, 24B, 26A, 26B), and counter rotation of the bobbins (24A, 24B, 26A, 26B) clamps the tube 18 between the bobbins (24A, 24B, 26A, 26B) in the tapered grooves (30). The clamp arrangement allows tubes of different shapes and diameters to be securely held without overly deforming the tube.

8 Claims, 4 Drawing Sheets

(51) Int. Cl.
*F16K 7/04* (2006.01)
*F16K 35/10* (2006.01)

(52) U.S. Cl.
CPC .......... *A61M 39/286* (2013.01); *F04B 43/12* (2013.01); *F16K 7/04* (2013.01); *F16K 35/10* (2013.01)

(56) References Cited

U.S. PATENT DOCUMENTS

| | | | |
|---|---|---|---|
| 4,179,249 A | 12/1979 | Guttmann | |
| 6,957,798 B1* | 10/2005 | Schmidt | F16K 7/065 251/6 |
| 7,322,556 B2* | 1/2008 | Bernstein | F16K 7/063 251/4 |
| 7,478,999 B2* | 1/2009 | Limoges | F04B 43/1253 417/474 |
| 7,565,918 B2* | 7/2009 | Zamalis | F16K 5/0407 138/45 |
| 2002/0131881 A1* | 9/2002 | Kagawa | F04B 9/02 417/477.1 |
| 2004/0267305 A1 | 12/2004 | Borgman | |
| 2007/0020130 A1* | 1/2007 | Malbec | F04B 43/1253 417/477.9 |
| 2010/0130920 A1 | 5/2010 | Lo et al. | |
| 2011/0314977 A1 | 12/2011 | Lewis | |
| 2013/0315763 A1* | 11/2013 | Neoh | F04B 43/1261 417/474 |
| 2015/0190628 A1 | 7/2015 | Kim et al. | |
| 2016/0106630 A1* | 4/2016 | Hudson | A61M 5/16831 700/282 |
| 2019/0001047 A1* | 1/2019 | Turner | A61M 1/3653 |

FOREIGN PATENT DOCUMENTS

| | | |
|---|---|---|
| JP | 59-176481 A | 10/1984 |
| WO | WO 2013/191335 A1 | 12/2013 |

OTHER PUBLICATIONS

Frédéric Neiller, Authorized Officer European Patent Office, International Search Report—Application No. PCT/GB2016/050044, dated Mar. 8, 2016, 11 pages, together with the Written Opinion of the International Searching Authority.

* cited by examiner

PUMP TUBE RETENTION MECHANISM

FIELD OF THE INVENTION

The present invention relates to a roller pump tube retention mechanism. Particularly, the present invention relates to an improved system and method for retaining a tube in a roller pump system.

BACKGROUND TO THE INVENTION

In many cases it may be desirable when pumping fluid to avoid the fluid coming into contact with pumping components etc. This can avoid cross-contamination and keep the pumped fluid clean and sterile. This is particularly important in cases such as circulating blood for a patient undergoing surgery. A roller, or peristaltic, pump can be used in these circumstances.

FIG. 1 shows an example prior art roller pump 1 used to pump fluid, such as blood. The roller pump 1 utilises a flexible tube 2 in a circular portion of a housing 3 with a number of rotating rollers 4 housed on a rotor 5. These rollers 4 squeeze the fluid along the tube 2 in a continuous motion. The rollers 4 exert a force on the tube 2 which requires it to be firmly held at the entry 6A and exit 6B positions of the housing 3 to prevent the tube 2 "walking" through the roller pump 1 during continuous use. The restraining force that is required increases for higher pump speeds or pump pressures. The rotor 5 rotates clockwise, as viewed from above in FIG. 1, with the rollers 4 making contact and moving around the tube 2 accordingly. The tube 2 is constricted between the rollers 4 and the housing 3 as the rollers 4 rotate and this moves the fluid along the tube 2 in the direction of the arrows as indicated.

The outer diameter of the tube may be chosen depending on the current setup of the pump and the fluid it is pumping. A particular pump can take several different sizes of tube. Some existing pumps use features, e.g. grippers 7, which deform the tube in order to grip it—see FIG. 2. Others make use of removable inserts 8, 9, to enable different sizes of tube to be gripped—see FIGS. 3 and 4. Both of these methods are undesirable for different reasons, one puts a strain on the tube and also restricts the fluid flow within the tube. The other requires a library of parts to be able to fit different tube sizes, and the inserts 8, 9, must be removed and refitted.

The present invention has therefore been devised with the foregoing in mind. The invention seeks to overcome or ameliorate at least one of the disadvantages of the prior art, or provide a useful alternative.

SUMMARY OF THE INVENTION

According to a first aspect of the present invention there is provided a clamp arrangement for retaining a flexible tube during operation of a roller pump for pumping fluid, the clamp arrangement comprising a pair of rotatable bobbins mounted adjacent to each other, wherein each bobbin has a tapered groove, formed partially around a cylindrical surface of the bobbin, and whereby counter rotation of the bobbins clamps the tube between the bobbins in the tapered grooves. This has the advantage that the tube is prevented from "walking", i.e. moving out of the roller pump housing, as the roller pump is operated. Further, tubes of different shapes and diameters can be securely held without overly deforming the tube, and thus restricting fluid flow, or requiring parts to be removed and refitted.

The cross sectional size of the tapered groove of one bobbin may match the cross sectional size of the tapered groove of the other bobbin. The advantage of this is that the tube is clamped by both grooves equally without non-symmetrical gaps between the tube and the grooves. This means that one section of the tube around its circumference is not clamped or constricted more than another section of the tube.

The tapered grooves of each of the bobbins may have a semi-circular cross section. This has the advantage that a circular tube can be held by the grooves around its full circumference.

The diameter of the tapered groove of one bobbin may match the diameter of the tapered groove of the other bobbin.

The diameter of each groove may steadily decrease around the partial circumference of the bobbin from a largest diameter to a smallest diameter. The advantage of this is that the bobbins can be rotated to accommodate any tubes with diameters from the largest diameter to the smallest diameter of the grooves.

The bobbins may be configured to counter rotate at the same rate to steadily reduce the size of the opening. This has the advantage that the size of the opening between the tubes is symmetrical at all times and a user can determine when the bobbins have been rotated by the optimum amount.

One of the bobbins may have the tapered groove tapering in a clockwise direction and the other bobbin may have the tapered groove tapering in an anticlockwise direction. This has the advantage that as the bobbins are counter rotated the opening between the grooves is increased or decreased as required.

The clamp arrangement may further comprise a locking mechanism configured to stop the rotation of the bobbins in the direction which enlarges the opening. The advantage of this is that the tube cannot be released or loosened unintentionally once the clamp has been tightened around the tube and locked.

The locking mechanism may comprise a ratchet or a locking handle.

The bobbins may be configured to tighten around the tube when the tube is under tension from the roller pump. This has the advantage that the tube is not pulled through the clamp when the roller pump is functioning.

The clamp arrangement may further comprise another pair of said bobbins. The advantage of this is that stretching of the tube out of the housing is prevented and fluid flow can be reversed in the tube with the tube still being held securely by the bobbins.

The tube may pass through one pair of bobbins before entering a housing of the roller pump and may pass through the other pair of bobbins upon exiting the housing. This has the advantage that the tube is held at both ends protruding from the housing which means movement and stretching of the tube is minimised compared to having a single pair of bobbins.

According to a second aspect of the present invention there is provided a roller pump for pumping fluid around a flexible tube comprising a clamp arrangement as described above. This has the advantage that the roller pump is capable of fitting a wide variety of tube diameters without unduly restricting flow, and causing excessive degradation of the flexible tubes. Also, the system can quickly be changed to accommodate different sizes of tubes without having to add or remove pieces, which reduces time and associated cost.

BRIEF DESCRIPTION OF THE INVENTION

An embodiment of the invention will now be described, by way of example only, with reference to the accompanying drawings in which.

DESCRIPTION OF THE EMBODIMENTS OF THE INVENTION

Figure 5:
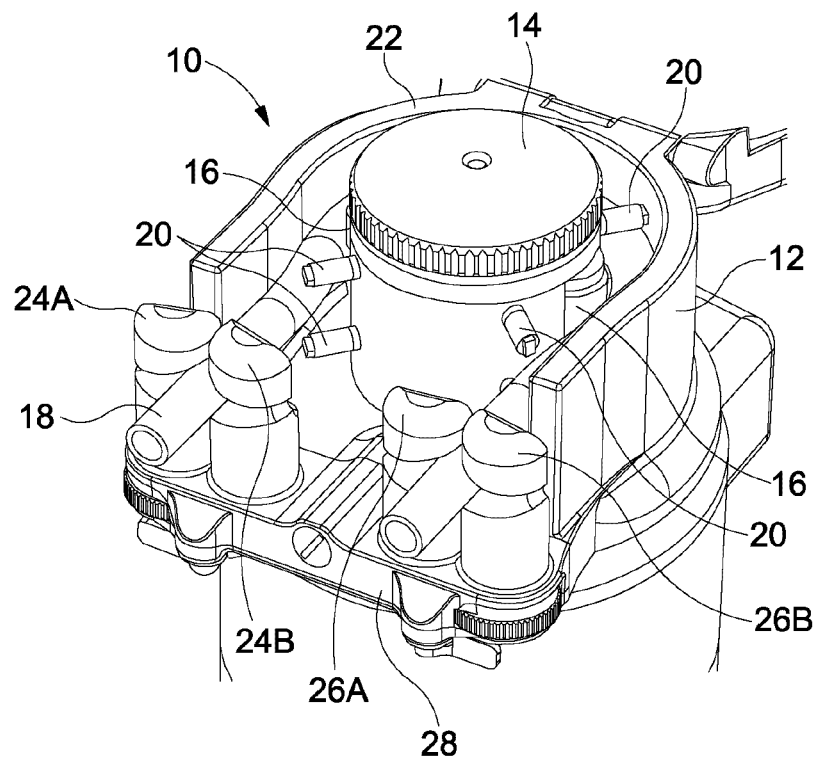
FIG. 5 shows a perspective view of a roller pump with a clamp system in accordance with an embodiment of the present invention.

With reference to FIG. 5, there is shown a roller pump 10 comprising a housing 12, a rotor 14 and rollers 16. The rotor 14 is located within the housing 12 and a flexible tube 18 is fed around the rotor 14, between the rotor 14 and the housing 12. The rotor 14 is substantially cylindrical and extends longitudinally which, for ease of description, shall be called the vertical direction. The housing 12 has extending vertical walls being substantially parallel to the longitudinal sides of the rotor 14. The tube 18 is located around the housing 12 at approximately the vertical mid-point of the housing 12. Arms 20 connected to the rotor 14 are used to locate the tube 18 in position. The housing 12 comprises a part-circular portion 22 which follows the curvature of the rotor 14 and thus maintains an approximate same distance between the inner walls of the housing 12 and the sides of the rotor 14. This allows the rollers 16 to also maintain an approximate same distance to the inner walls of the housing 12 which enables the rotor 14 and rollers 16 to make a relatively consistent compression of the flexible tube 18 as they rotate.

Where the tube 18 enters and exits the roller pump 10, there is provided two pairs of bobbins 24A, 24B, 26A, 26B. The first pair of bobbins 24A, 24B, are touching or almost touching each other and the second pair of bobbins 26A, 26B, are touching or almost touching each other. The tube 18 passes through an opening 28A formed from a pair of substantially semi-circular slots or grooves 30, one in each of the first pair of bobbins 24A, 24B. The grooves 30 have a semi-circular cross section. This will conventionally be called the entry, i.e. the direction of the fluid, e.g. blood, is towards the roller pump 10 at this point when it is being pumped. The tube 18 also passes through a similar opening 28B in the second pair of bobbins 26A, 26B. This will conventionally be called the exit, i.e. the direction of the fluid, e.g. blood, is away from the roller pump 10 at this point when it is being pumped. The pair of bobbins 24A, 24B form a LHS clamp 25 and the pair of bobbins 26A, 26B form a RHS clamp 27. The clamps 25, 27, work to hold the tube 18 in place, which will be described in more detail later.

The current embodiment has two pairs of bobbins 24A, 24B, 26A, 26B, which act to stop the tube 18 "walking" around the roller pump 10 and being stretched out of the housing 12. This also means that the fluid flow can be reversed in the tube 18 and the tube 18 would still be held in the roller pump 10. However, in other embodiments, only one pair of bobbins may be used to clamp the tube 18.

The bobbins 24A, 24B, 26A, 26B are housed on a mount 32 which holds the bobbins 24A, 24B, 26A, 26B, in place and allows them to freely rotate. The mount 32 is connected to the front portion of the housing 12. The bobbins 24A, 24B, 26A, 26B are positioned in a line, which is perpendicular to the direction of flow of blood into and out of the roller pump 10. The two bobbins 24A, 24B, are interlinked so that they rotate with respect to one another. The two bobbins 26A, 26B are similarly interlinked.

Figure 6:
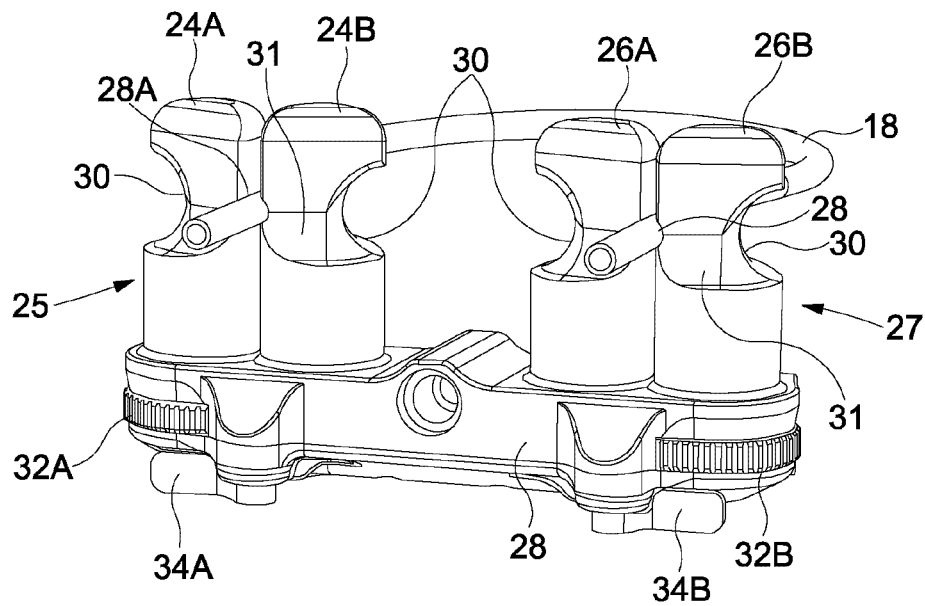
FIG. 6 shows a front view of a clamp system in accordance with the embodiment of FIG. 5.
Figure 7:
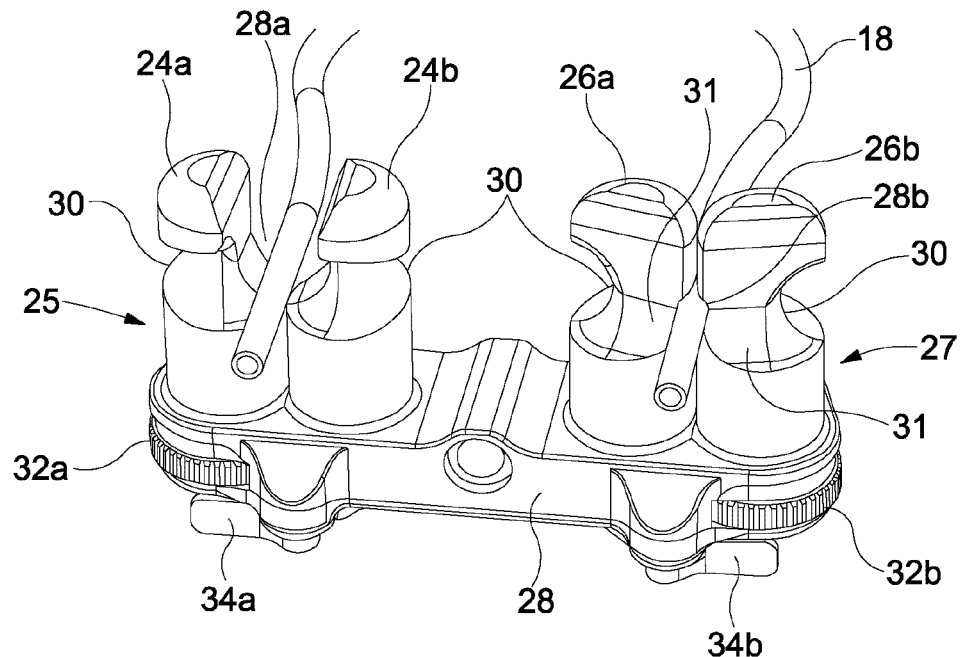
FIG. 7 shows a perspective view of a clamp system in use in accordance with the embodiment of FIG. 5.

The grooves 30 in the bobbins 24A, 24B, 26A, 26B are profiled to allow a range of tube 18 sizes to be accommodated. The profiles are shown in FIGS. 6 and 7 such that the semi-circular grooves 30 have steadily decreasing diameters formed around the circumference of the bobbins 24A, 24B, 26A, 26B. When viewed from above, the bobbins 24A, 26A, have the semi-circular groove 30 decreasing from the largest diameter to the smallest diameter in a clockwise direction. When viewed from above, the bobbins 24B, 26B, have the semi-circular groove 30 decreasing from the largest diameter to the smallest diameter in an anticlockwise direction.

The bobbins 24A, 24B, are orientated such that where they are closest to each other; the slots are of the same size. This, in addition to the bobbins 24A, 24B, touching or almost touching each other, means that the opening 28A formed by the grooves 30 is always circular. The situation is the same for bobbins 26A, 26B and opening 28B.

There is a smaller portion of the circumference of the bobbins 24A, 24B, 26A, 26B, between where the semi-circular groove 30 has the largest diameter and where the semi-circular groove 30 has smallest diameter, where there is not a steady change in size but a discontinuity. This discontinuity is in the form of a flatter section 31 located nearer the full diameter of the bobbins 24A, 24B, 26A, 26B.

The mount 32 comprises sprockets 32A and 32B to rotate the bobbins 24A, 24B, 26A, 26B, and locking handles 34A, 34B, which can be turned to hold the bobbins 24A, 24B, 26A, 26B, in the required position. The user manually determines when the bobbins 24A, 24B, 26A, 26B have been rotated enough to hold the tube 18 tightly and the locking handles 34A, 34B can be turned to lock or release the bobbins 24A, 24B, 26A, 26B. In other embodiments, an automated system including a sensor could be used to detect when the tube 18 has been clamped tight enough which then automatically locks the bobbins.

The tube 18 must be held at the entry and exit points otherwise as the rotor 14 turns and the rollers 16 compresses the tube 18 to pump the fluid, the tube 18 will move, or "walk" around the housing 12 which is undesirable. This could lead to the tube 18 being pulled out of accompanying components or cause a blockage in the tube 18. The current invention overcomes some of the limitations of prior art clamps used in roller pumps and provides an improved system.

Referring now to FIG. 7, it is shown that the tube 18 can be introduced through openings 28A, 28B between the corresponding bobbins 24A, 24B, 26A, 26B. In particular, referring to the bobbins 24A, 24B, of the LHS clamp 25, they are shown in their fully open position, i.e. where the semi-circular groove 30 are directly facing each other at their largest diameter. This gives the largest spacing between the two bobbins 24A, 24B. The bobbins 24A, 24B, are fully rotated to get to this position, i.e. bobbin 24A is fully rotated anticlockwise and bobbin 24B is fully rotated clockwise. As the bobbins 24A, 24B, are interlinked they are each rotated by the same amount and therefore have the same sized semi-circular groove 30 facing each other. In other embodiments, the bobbins 24A, 24B, do not need to be fully rotated to fit the tubes 18 as the outer diameters of the tubes 18 are small enough to fit into smaller openings 28A, 28B, between the bobbins 24A, 24B.

Figure 1:
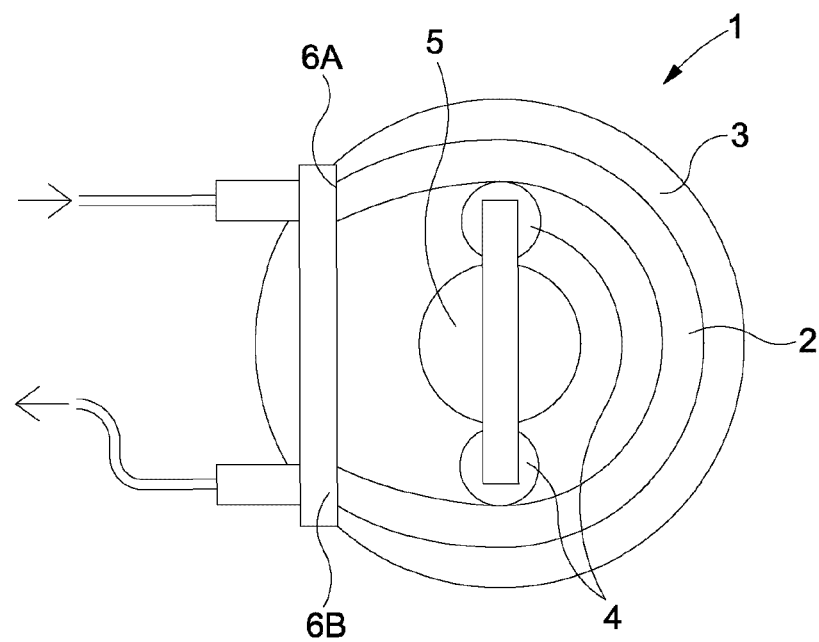
FIG. 1 shows a schematic top view of a known roller pump design.
Figure 2:
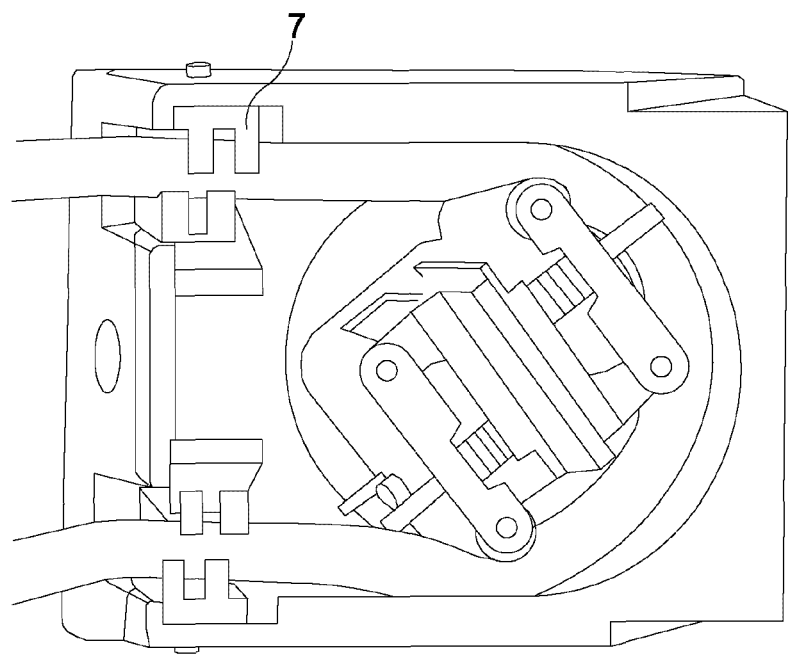
FIG. 2 shows a top view of a known roller pump.
Figure 3:
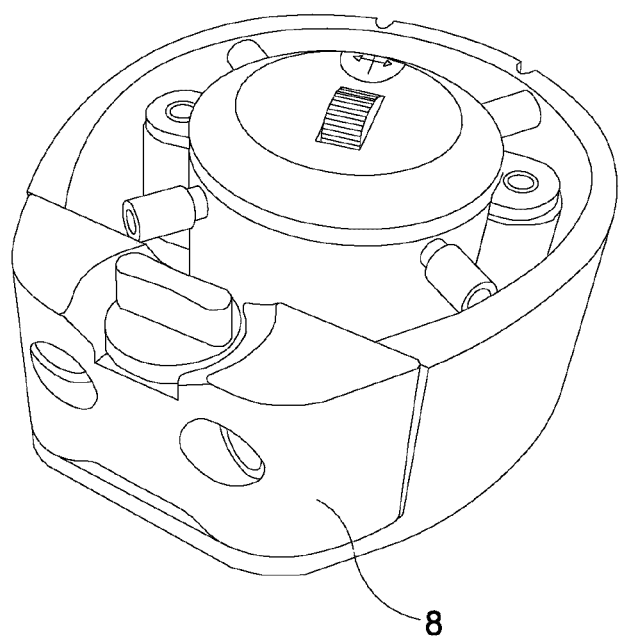
FIG. 3 shows a top view of another known roller pump.
Figure 4:
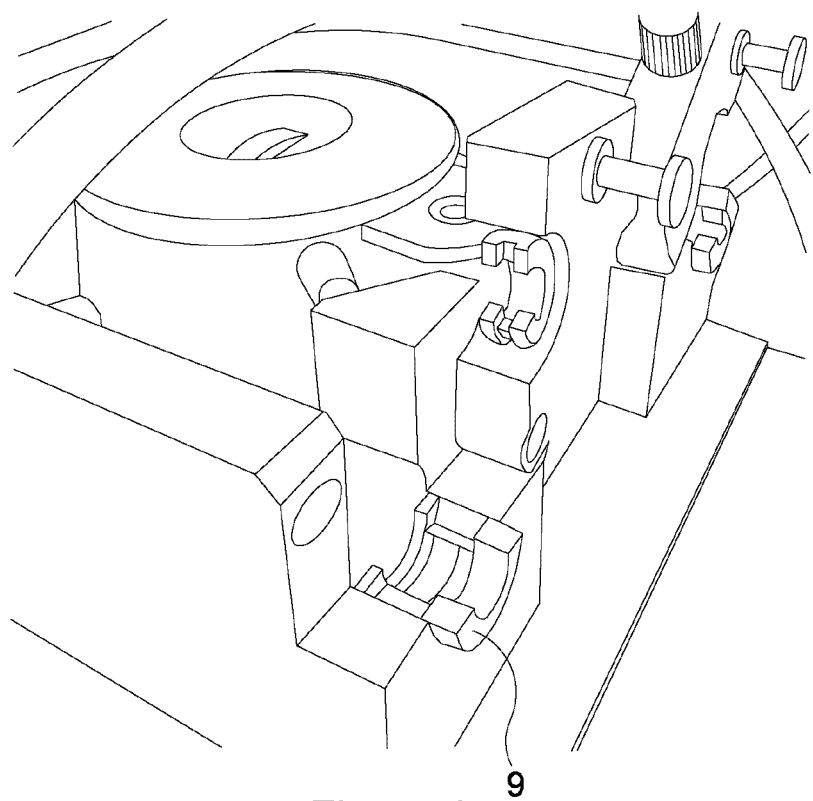
FIG. 4 shows a top view of another known roller pump.

Once the tube 18 is located centrally between the bobbins 24A, 24B, the bobbins are rotated in opposite directions. That is, bobbin 24A is rotated clockwise and bobbin 24B is rotated anticlockwise. This rotation, and the shape of the profiles of the bobbins 24A, 24B, as described above, means that the opening 28A reduces in effective diameter. A locking mechanism in the form of an anti-rotation ratchet (not shown) is provided to prevent the bobbins 24A, 24B, from rotating in reverse and thus avoiding the tube 18 being released. The locking handle 34A must be released to allow the bobbins 24A, 24B, to rotate to free the tube 18. In other embodiments, once the tube 18 is gripped by the circular opening 28A, i.e. clamped between the two bobbins 24A, 24B, then a locking mechanism is engaged by turning the locking handle 34A. The RHS clamp 27 shows the tube 18 clamped in place. It can be seen that the bobbins 26A, 26B, have been rotated as described above such that there is a small circular opening 28A between the bobbins 26A, 26B, which securely holds the tube 18 in position. In this case, the bobbins 26A, 26B, have not been fully rotated to make the smallest diameters of the groove 30 face each other. Instead, they have been stopped using the locking mechanism as the optimum position for holding the tube 18 without undue deformation has been reached. This is in contrast to the prior art roller tube grippers of FIG. 2 which can be seen to visibly deform the tube.

Figure 8:
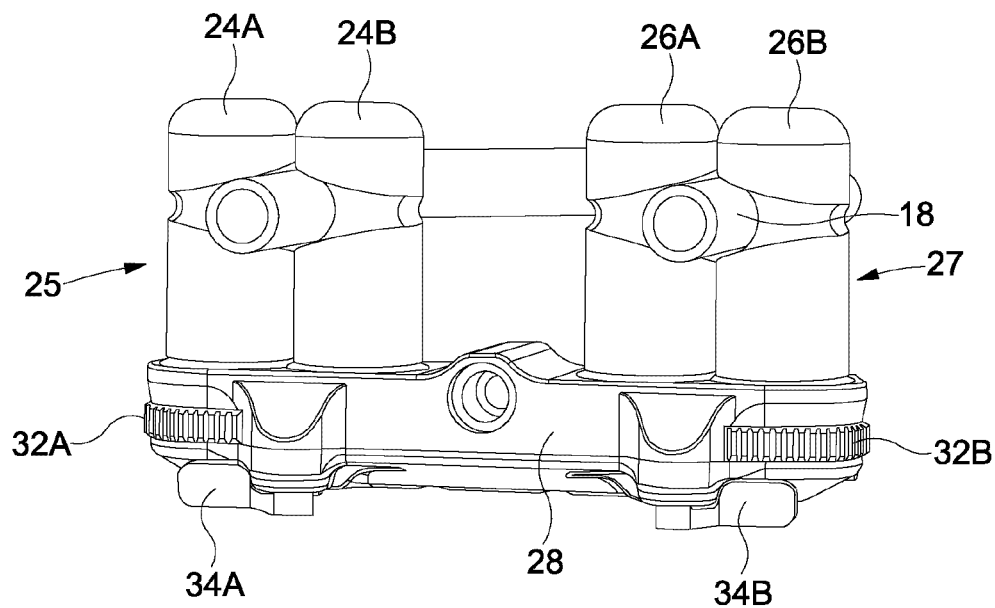
FIG. 8 shows a front view of a clamp system with a larger tube diameter in accordance with the embodiment of FIG. 5.

FIG. 8 shows a larger diameter tube 18 being clamped following the same procedure as described in relation to FIG. 7. This illustrates that different sized tubes 18 can be accommodated without unduly deforming them or having to modify the clamps by adding and removing pieces specific to the tube sizes.

When the roller pump 10 is operated the rollers 16 will place the tube 18 in tension and try to pull it through the bobbin clamps 25, 27. This will draw the clamps 25, 27, tighter around the tube 18 and resist movement of the tube 18. This is because, the orientation of the bobbins 24A, 24B, and their respective rotations, is such that tension on the tube 10 acting to move the tube 18 further into the roller pump 10 from the entry point rotates the bobbin 24A anticlockwise and the bobbin 24B clockwise which makes the opening 28A between the bobbins 24A, 24B slightly smaller. However, because the tube 18 is always clamped in a circular opening 28A, the tube 18 will not be pinched, as can occur in prior art clamping arrangements. The situation is similar for clamp 27, however it is tension acting to move the tube 18 further into the roller pump 14 from the exit point of the roller pump 14 that provides the rotation of the bobbins 26A, 26B to tighten the opening 28B. The movement of the bobbins 24A, 24B, 26A, 26B, in this tightening fashion due to tension is possible because, even though a locking mechanism is in place as described above, this locking mechanism acts only to stop rotation of the bobbins 24A, 24B, 26A, 26B, that produces a larger opening 28A, 28B.

It is clear from the above description that the current invention provides a system which is capable of fitting a wide variety of tube diameters without unduly restricting flow, and causing excessive degradation of the flexible tubes. Also, the system can quickly be changed to accommodate different sizes of tubes without having to add or remove pieces, which reduces time and associated cost.

It will be appreciated by persons skilled in the art that various modifications may be made to the above embodiment without departing from the scope of the present invention as defined by the claims. For example, whilst the above discussion has been concerned with pumping blood around a tube for use in a surgical procedure, the invention is equally applicable pumping other fluids such as slurries, chemicals or dangerous substances.

In addition, while the above discussion has described the more likely case of circular tubes, non-circular tubes may also be used in embodiments of the invention. For example, oval shaped tubes may be used and the grooves of the bobbins may be shaped so as to accommodate the oval tubes and perform a similar retaining function as that described above.

The invention claimed is:

1. A clamp arrangement for retaining a flexible tube during operation of a roller pump for pumping fluid, the clamp arrangement comprising:
    a pair of rotatable bobbins mounted adjacent to each other; and
    a locking mechanism configured to stop the rotation of the bobbins in the direction which enlarges an opening;
    wherein each bobbin of the pair of rotatable bobbins has a tapered groove, formed partially around a cylindrical surface of the bobbin, with the tapered groove of said each bobbin having a diameter steadily decreasing from a largest diameter to a smallest diameter, and wherein one of the bobbins has the tapered groove tapering in a clockwise direction and the other of the bobbins has the tapered groove tapering in an anticlockwise direction;
    wherein the bobbins are configured to tighten around the tube when the tube is under tension from the roller pump;
    whereby counter rotation of the bobbins clamps the tube between the bobbins in the tapered grooves;
    wherein the tapered grooves of said each of the bobbins have a semi-circular cross section along the length of the tapered groove from the largest diameter to the smallest diameter.

2. The clamp arrangement according to claim 1, wherein the cross sectional size of the tapered groove of the one of the bobbins matches the cross sectional size of the tapered groove of the the other of the bobbins.

3. The clamp arrangement according to claim 1, wherein the diameter of the tapered groove of the one of the bobbins matches the diameter of the tapered groove of the other of the bobbins.

4. The clamp arrangement according to claim 1, wherein the bobbins are configured to counter rotate at the same rate to steadily reduce the size of the opening.

5. The clamp arrangement according to claim 1, wherein the locking mechanism comprises at least one selected from the group consisting of a ratchet and a locking handle.

6. The clamp arrangement according to claim 1, further comprising another pair of said bobbins.

7. The clamp arrangement according to claim 6, wherein the tube passes through the pair of bobbins before entering a housing of the roller pump and passes through the other pair of bobbins upon exiting the housing.

8. A roller pump for pumping fluid around a flexible tube comprising:
    a clamp arrangement configured to retain the flexible tube during operation of the roller pump, the clamp arrangement including:
    a locking mechanism;

a pair of rotatable bobbins mounted adjacent to each other, each bobbin of the pair of rotatable bobbins having a tapered groove formed partially around a cylindrical surface of the bobbin with the tapered groove of said each bobbin having a diameter steadily decreasing from a largest diameter to a smallest diameter, one of the bobbins having the tapered groove tapering in a clockwise direction and the other of the bobbins having the tapered groove tapering in an anticlockwise direction, wherein the bobbins are configured to tighten around the tube when the tube is under tension from the roller pump;

whereby counter rotation of the bobbins clamps the tube between the bobbins in the tapered grooves;

wherein the tapered grooves of said each of the bobbins have a semi-circular cross section along the length of the tapered groove from the largest diameter to the smallest diameter; and wherein the locking mechanism is configured to stop the rotation of the bobbins in the direction which enlarges the opening.

\* \* \* \* \*